(12) United States Patent
Dolitzky

(10) Patent No.: US 6,852,855 B2
(45) Date of Patent: Feb. 8, 2005

(54) SYNTHESIS OF PIPERAZINE RING

(75) Inventor: Ben-Zion Dolitzky, Petach Tiqva (IR)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 0 days.

(21) Appl. No.: 09/939,406

(22) Filed: Aug. 24, 2001

(65) Prior Publication Data

US 2002/0035256 A1 Mar. 21, 2002

Related U.S. Application Data

(63) Continuation of application No. 09/545,011, filed on Apr. 7, 2000, now Pat. No. 6,339,156.
(60) Provisional application No. 60/130,048, filed on Apr. 19, 1999.

(51) Int. Cl.$^7$ ................ C07D 487/14; C07D 241/04
(52) U.S. Cl. ................ 540/578; 544/360; 544/383; 544/384; 544/391
(58) Field of Search .................. 544/383, 382, 544/385, 403, 360, 384, 386, 391; 540/578

(56) References Cited

U.S. PATENT DOCUMENTS

| | | | |
|---|---|---|---|
| 2,507,408 A | | 5/1950 | Jacob |
| 2,830,056 A | | 4/1958 | Ruschig et al. |
| 2,891,063 A | | 6/1959 | Sommers |
| 3,663,548 A | | 5/1972 | Nitta et al. |
| 4,025,513 A | | 5/1977 | Olivie |
| 4,062,848 A | | 12/1977 | van der Burg |
| 4,217,452 A | * | 8/1980 | Olivie |
| 4,912,110 A | * | 3/1990 | Lafon |
| 4,918,190 A | * | 4/1990 | Toda et al. ............ 544/383 |
| 4,935,515 A | * | 6/1990 | Winkley et al. ......... 540/554 |
| 6,339,156 B1 | * | 1/2002 | Dolitzky |

FOREIGN PATENT DOCUMENTS

HU 174 215 11/1979

OTHER PUBLICATIONS

Nickolson et al., J. Pharm. Pharmacol. 33, pp. 760–766 (1981).*

Nishimura et al., Chem. Pharm.Bull., vol. 17, p94–97 (1969).*

Roderick, W.R. et al., J. Med. Chem, 1966, vol. 9, pp. 181–185.

Database Crossfire Beilstein Online! Beilstein Institut zur Forderung der Chemischen Wissenschaften, Frankfurt am Main, DE; Database accession No. 1584167 XP002196248 1–p–Toluolsulfonyl–2, 4–dimethyl–piperazine * abstract* for Chem Pharm Bull, vol. 17, No. 1, 1969, p. 94ff, Nishimura.

Fujimura et al: "Synthesis, Structure and quantitative Structure–Activity Relationships of sigma receptor Ligands, 1–2–(3,4–Dimethoxyphenyl)ethyl !–4–(3–phenylpropyl)piperazines" Bioorganic & Medicinal Chemistry, vol. 5, No. 8, 1997, pp. 1675–1683, XP002196245 Reaction of 4 and 5 on *p. 1676*.

Chemical Abstracts, vol. 71, No. 21, Nov. 24, 1969 Columbus, Ohio, US; abstract No. 101885, Nitta, Yoshihiro et al: "Piperazine derivatives and their salts" XP002196247 *abstract* & JP 44 018306 B (Chugai Pharmaceutical Co., Ltd.) Aug. 11, 1969.

* cited by examiner

*Primary Examiner*—Emily Bernhardt
(74) *Attorney, Agent, or Firm*—Kenyon & Kenyon

(57) ABSTRACT

A novel process for preparing a compound of the formula I:

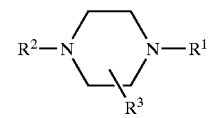

wherein $R^1$ denotes substituted or unsubstituted alkyl, alkoxy, aryl, aryloxy or arylalkoxy; $R^2$ denotes substituted or unsubstituted alkyl, alkoxy, aryl, aryloxy, arylalkoxy, tosyl, formyl, acetyl or amine; and $R^3$ denotes substituted or unsubstituted alkyl, alkoxy, aryl, aryloxy or arylalkoxy is disclosed. These compounds are useful in the synthesis of the antidepressant mirtazapine and other tetracyclic compounds.

26 Claims, No Drawings

SYNTHESIS OF PIPERAZINE RING

RELATED APPLICATION

This application is a continuation of application Ser. No. 09/545,011, filed Apr. 7, 2000, now U.S. Pat. No. 6,339,156, which claims the benefit under 35 U.S.C. § 119(e) of U.S. Provisional Application Ser. No. 60/130,048, filed Apr. 19, 1999.

FIELD OF THE INVENTION

The present invention relates to methods for the synthesis of piperazine rings, particularly for the preparation of heterocyclic compounds useful as intermediates in the synthesis of piperazinoazepines such as the antidepressant mirtazapine.

BACKGROUND OF THE INVENTION

Mirtazapine, also known as 1,2,3,4,10,14b-hexahydro-2-methylpyrazine [2,1-a]pyrido[2,3-c]benzazepine, is an antidepressant suitable for oral administration. It has a tetracyclic chemical structure unrelated to other classes of antidepressants such as selective seratonin reuptake inhibitors (SSRIs), tricyclics or monoamine oxidase inhibitors. Mirtazapine belongs to the piperazinoazepine group of compounds, and has the following structural formula

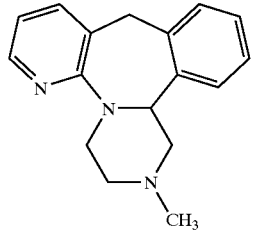

Known methods for the preparation of piperazine ring derivatives have low yields (9–30%), expensive reagents, and many reaction steps (Roderick, W. R. et al., J. Med. Chem 9, 1966, 181–185). It is desirable to have methods for preparing piperazine ring derivatives with fewer steps, high yields and inexpensive raw materials.

SUMMARY OF THE INVENTION

The present invention relates to a novel process for preparing a compound of the formula

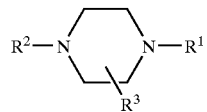

wherein $R^1$ denotes substituted or unsubstituted alkyl, aryl, arylalkoxy, tosyl, formyl, benzoyl, acetyl or amine; $R^2$ denotes substituted or unsubstituted alkyl, alkoxy, aryl, aryloxy or arylalkoxy; land $R^3$ denotes substituted or unsubstituted alkyl, alkoxy, aryl, aryloxy or arylalkoxy; by reacting a compound of the formula

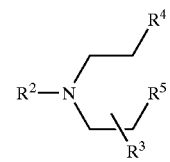

II wherein $R^2$ and $R^3$ are as defined above and $R^4$ and $R^5$ are independently selected from the group consisting of fluoro, chloro, bromo and iodo, with a compound of the formula $H_2N-R^1$, wherein $R^1$ is as defined above. Preferably the reaction is performed in the presence of a solvent. Polar aprotic solvents such as, dimethyl formamide, dimethylacetamide and dimethylsulfoxide are preferred.

DETAILED DESCRIPTION OF THE INVENTION

The present invention provides a new process for preparing piperazine rings suitable for use in the synthesis of the antidepressant mirtazapine and other tetracyclic compounds such as those disclosed in U.S. Pat. No. 4,062,848 to van der Burg, the contents of which are incorporated herein by reference.

The process of the present invention comprises the steps of reacting a compound of formula II:

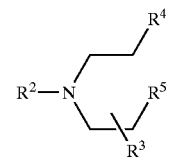

II wherein $R^4$ and $R^5$ are independently any of the of radicals selected from the group that consists of fluoro, chloro, bromo and iodo; and $R^2$ and $R^3$ are as defined above; with a compound of the formula $H_2N-R^1$, wherein $R^1$ is as defined above. Preferably, $R^1$ denotes aryl, acetyl, formyl, benzoyl, amine, or tosyl. Most preferably, $R^1$ is tosyl. In order to remove any doubt, the tosyl radical is defined as the group of formula VI:

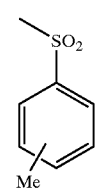

VI wherein Me represents a methyl group. Preferably $R^2$ denotes methyl, $R^3$ denotes phenyl, $R^4$ denotes chloro, and $R^5$ denotes chloro.

Preferably, the compounds of formulae I and II are compounds of formulae IV and V accordingly:

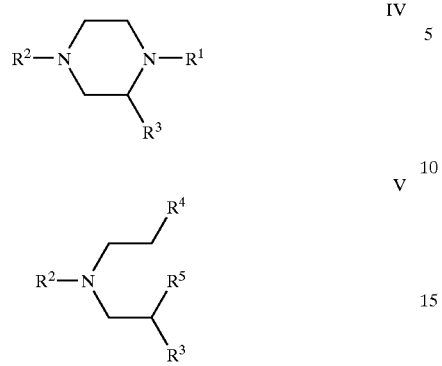

In a preferred embodiment, the present invention relates to a process for preparing a compound of formula XI:

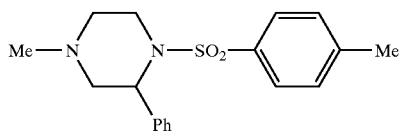

wherein Ph represents a phenyl group, which comprises reacting a compound of formula XII:

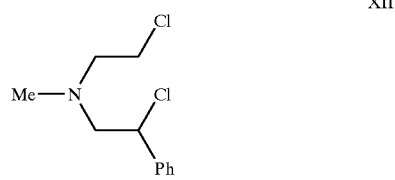

with a compound of formula XIII:

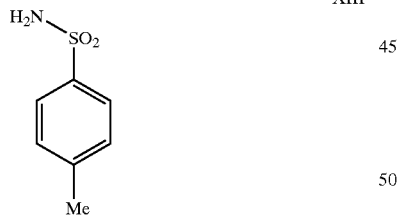

Preferably this reaction takes place in the presence of a strong base such as sodium hydroxide (NaOH), sodium hydride (NaH), potassium hydroxide (KOH), potassium hydride (KH), sodium methoxide (NaOMe) and sodium amide ($NaNH_2$). Sodium hydroxide and sodium hydride are preferred.

Preferred solvents for the above reaction are any one or more of the solvents selected from the group that consisting of dimethyl formamide (DMF), dimethyl acetamide (DMAC), dimethyl sulfoxide (DMSO), xylene, benzene, ethylbenzene, acetonitrile, toluene and ethers with high boiling points such as ethyleneglycol dimethyl ether, diethyleneglycol dimethyl ether, and propyleneglycol dimethyl ether.

The compound of formula XI may be further hydrolized to give the compound of formula XIV:

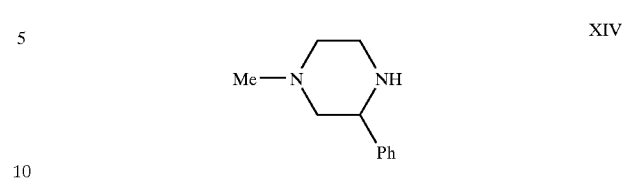

The compound of formula XIV is known as 4-methyl-2-phenylpiperazine. Compounds of formula XI may be hydrolyzed by reacting a compound of the formula XI with acid to give compounds of the formula XIV. Preferred acids for the reaction are strong acids such as sulfuric acid ($H_2SO_4$), hydrochloric acid (HCl), phosphoric acid ($H_3PO_4$) and p-toluene sulfonic acid. A more preferred acid is sulfuric acid with a concentration of about 98%. Preferably the reaction is carried out in aqueous solution.

The compound of formula XIV may be used in the preparation of the mirtazapine (1,2,3,4,10,14b-hexahydro-2-methyl-pyrazino[2, 1-a]pyrido[2,3-c][2] benzazepine), as shown in Schemes 1 and 2 below.

Scheme 1

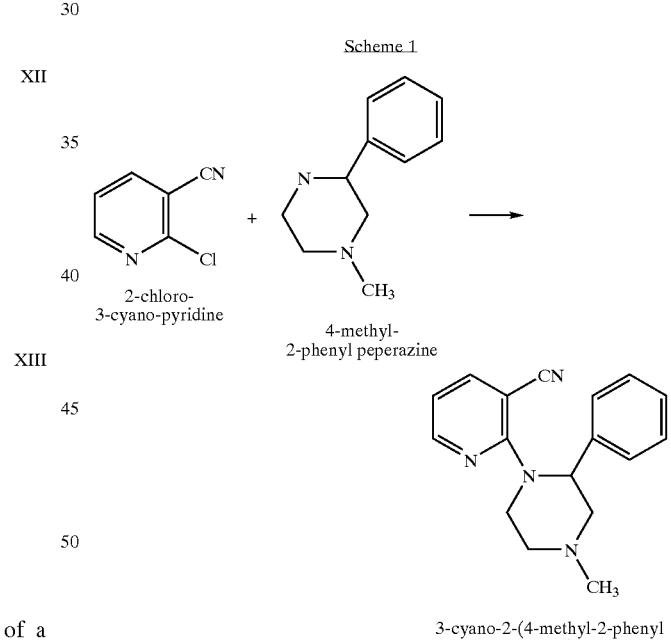

As shown in Scheme 1, the compound 3-cyano-2(4-methyl-2-phenyl-1-piperazynyl) pyridine may be prepared starting from 2-chloro-3-cyano pyridine and 4-methyl-2-phenyl-piperazine.

Starting from 3-cyano-2-(4-methyl-2-phenyl-1-piperazynyl)pyridine, mirtazapine can be prepared by two routes, which are further presented in Scheme 2:

Scheme 2

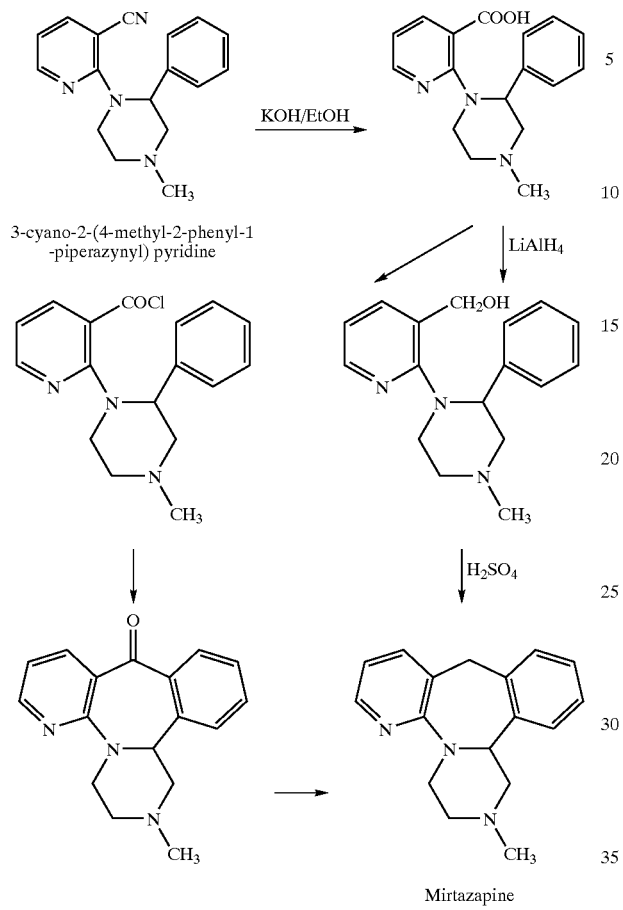

Mirtazapine

In accordance with the present invention, mirtazapine produced by the process of the present invention may be prepared as pharmaceutical compositions that are particularly useful for the treatment of depression. Such compositions comprise mirtazapine with pharmaceutically acceptable carriers and/or excipients known to one of skill in the art.

EXAMPLES

The following examples are given for the purpose of illustrating the present invention and shall not be construed as being limitations on the scope or spirit of the invention.

Example 1

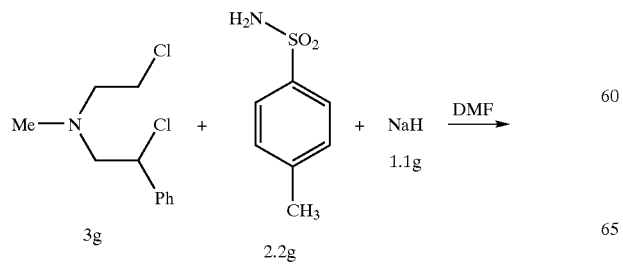

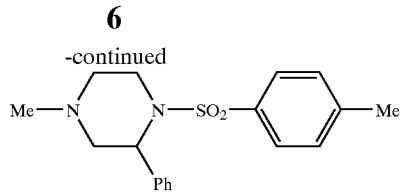

A suspension of sodium hydride (60%, 1.1 g) in DMF (20 mL) was prepared. p-Toluenesulfonamide (2.2 g) was dissolved in DMF (10 mL) and added continuously to the sodium hydride suspension. After mixing at room temperature the suspension was heated to 60–70° C.

After that, the solution of beta-chloro-N-methyl-N-chloroethyl phenylethylamine (3 g) in DMF (10 mL) was added dropwise and mixed overnight. The reaction mixture was poured into a mixture of water (21 g) and ice (40 g).

After 4 hours the precipitate was filtered, washed with water (2×30 mL) and dried in an oven to give 3.3 g of the product.

Example 2

Preparation f 4-methyl-2-phenyl piperazine

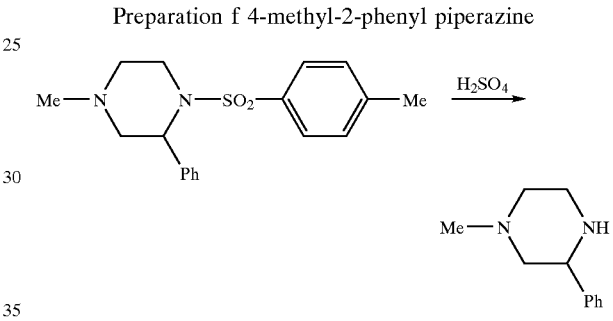

Tosyl piperazine (1.2 g) was dissolved in water (Ig) and $H_2SO_4$ (98%, 3 mL) while heating to 110° C. After 20 minutes at 110–120° C. the reaction mixture was poured into water (10 mL) and ice (20 g).

The solution was alkalized to pH 13 with NaOH (47%) and the product was extracted into ether. After phase separation the organic phase was evaporated to dryness to give the 4-methyl-2-phenyl piperazine in 75% yield.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

I claim:

1. A method for preparing a compound of the formula

IV

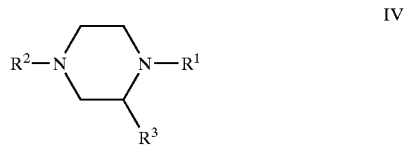

wherein $R^1$ denotes phenylalkoxy, tosyl, benzoyl, or formyl; $R^2$ denotes alkyl; and $R^3$ denotes phenyl, comprising the step of reacting a compound of the formula

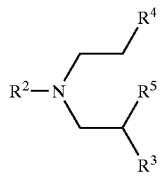

wherein $R^2$ and $R^3$ are as defined above and $R^4$ and $R^5$ are independently selected from the group consisting of fluoro, chloro, bromo and iodo, with a compound of the formula $H_2N-R^1$, wherein $R^1$ is as defined above.

2. The method of claim 1, wherein $R^1$ is selected from the group consisting of formyl, benzoyl, and tosyl.

3. The method of claim 1, wherein $R^1$ is tosyl.

4. The method of claim 1, wherein $R^2$ is methyl.

5. The method of claim 1, wherein $R^4$ is chloro.

6. The method of claim 1, wherein $R^5$ is chloro.

7. The method of claim 1, wherein the reaction is performed in a solvent selected from the group consisting of DMF, DMAC, ethers, ethyleneglycol dimethyl ether, diethyleneglycol dimethyl ether, propyleneglycol dimethyl ether, DMSO, xylene, benzene, ethylbenzene, acetonitrile and toluene.

8. The method of claim 7, wherein said solvent is DMF.

9. The method of claim 1, further comprising the step of adding a strong base.

10. The method of claim 9, wherein said strong base is selected from the group consisting of sodium hydroxide, sodium hydride, potassium hydroxide, potassium hydride, sodium methoxide and sodium amide.

11. The method of claim 10, wherein the base is sodium hydroxide.

12. The method of claim 10, wherein the base is sodium hydride.

13. The method of claim 1, further comprising the step of removing $R^1$ by hydrolysis.

14. The method of claim 13, wherein $R^1$ is removed by hydrolysis using a strong acid.

15. The method of claim 14, wherein the acid is selected from the group consisting of sulfuric acid, hydrochloric acid, phosphoric acid and p-toluene sulfonic acid.

16. The method of claim 15, wherein the acid is sulfuric acid.

17. The method of claim 16 wherein the sulfuric acid has a concentration of about 98%.

18. A compound of the formula:

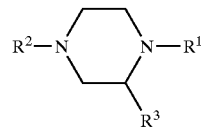

wherein $R^1$ denotes tosyl, formyl, or benzoyl; $R^2$ denotes methyl; and $R^3$ denotes phenyl.

19. A method for preparing 4-methyl-2-phenylpiperazine comprising hydrolyzing a compound of claim 18 using an acid.

20. The method of claim 19, wherein the acid is sulfuric acid.

21. A method for preparing 3-cyano-2-(4-methyl-2-phenyl-1-piperazinyl) pyridine comprising:

hydrolyzing a compound of claim 18 to form 4-methyl-2-phenylpiperazine; and reacting 4-methyl-2-phenylpiperazine with a 3-cyano-pyridine to form 3-cyano-2-(4-methyl-2-phenyl-1-piperazinyl) pyridine.

22. A method for preparing mirtazapine comprising the steps of:

hydrolyzing a compound of claim 18 to form 4-methyl-2-phenylpiperazine;

reacting 4-methyl-2-phenylpiperazine with a 3-cyano-pyridine to form 3-cyano-2-(4-methyl-2-phenyl-1-piperazinyl) pyridine;

converting 3-cyano-2-(4-methyl-2-phenyl-1-piperazinyl) pyridine to 3-carboxy-2-(4-methyl-2-phenyl-1-piperazinyl) pyridine; and converting 3-carboxy-2-(4-methyl-2-phenyl-1-piperazinyl) pyridine to mirtazapine.

23. A compound of the formula:

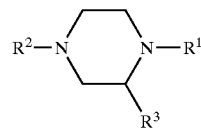

wherein $R^1$ denotes phenylalkoxy, tosyl, benzoyl, or formyl; $R^2$ denotes alkyl; and $R^3$ denotes phenyl.

24. The compound of claim 23, wherein $R^1$ is formyl, benzoyl, or tosyl.

25. The compound of claim 23, wherein $R^2$ is methyl.

26. The compound of claim 23, wherein $R^1$ is tosyl.

* * * * *